United States Patent [19]
Saper et al.

[11] Patent Number: 5,910,103
[45] Date of Patent: Jun. 8, 1999

[54] DEVICE AND METHOD FOR AN IAB ASSIST WITH MULTIPLE BALLOONS

[75] Inventors: Lawrence Saper, New York, N.Y.; Stanton Rowe, Englewood; Boris Ijeschinsky, Waldwick, both of N

[73] Assignee: Datascope Investment Corp., Montvale, N.J.

[21] Appl. No.: 08/880,625

[22] Filed: Jun. 23, 1997

[51] Int. Cl.⁶ .................................................. A61M 1/12
[52] U.S. Cl. ................................................................ 600/18
[58] Field of Search ............................. 600/16–18; 623/3

[56] References Cited

U.S. PATENT DOCUMENTS

| | | | |
|---|---|---|---|
| 4,527,549 | 7/1985 | Gabbay | 600/18 |
| 4,771,765 | 9/1988 | Choy et al. | 600/18 |
| 5,776,047 | 7/1998 | Fukunaga et al. | 600/18 |

*Primary Examiner*—William E. Kamm
*Assistant Examiner*—George R. Evanisko
*Attorney, Agent, or Firm*—J. Gary Mohr; Abraham Ronei

[57] ABSTRACT

A Device and method are provided to split a single chambered IAB device into at least two IAB distinct chambers, that work in conjunction with each other, each being smaller than the single chamber, but the combination of the two chambers may be greater than the single chamber.

7 Claims, 4 Drawing Sheets

MULTIPLE IAB BALLOONS: DIMENSIONS AND VOLUME CALCULATIONS FOR 15cc, 20cc, AND 25cc BALLOONS

| MEMBRANE DIAMETER, MIN. | MEMBRANE ID, IN | NECK DIAMETER, IN | OVERALL MEMBRANE LENGTH, IN | B. TAPERED LENGTH, IN | BALLOON VOLUME, CC | INNER LUMEN OD, IN | CATHETER OD, FR | |
|---|---|---|---|---|---|---|---|---|
| 8.92 | 0.351 | 0.065 | 10.2 | 0.5 | 15.05 | 0.033 | 6.0-6.5 | REGULAR LENGTH |
| 10.29 | 0.405 | 0.065 | 10.2 | 0.5 | 20.07 | 0.033 | 6.5-7.0 | |
| 11.48 | 0.452 | 0.065 | 10.2 | 0.5 | 25.03 | 0.033 | 7.0-7.5 | |
| 8.56 | 0.337 | 0.065 | 11 | 0.5 | 15.02 | 0.033 | 6.0-6.5 | LONGER BALLOONS |
| 9.88 | 0.389 | 0.065 | 11 | 0.5 | 20.05 | 0.033 | 6.5-7.0 | |
| 11.06 | 0.435 | 0.065 | 11 | 0.5 | 25.11 | 0.033 | 7.0-7.5 | |
| 9.53 | 0.375 | 0.065 | 9 | 0.5 | 15.04 | 0.033 | 6.0-6.5 | SHORTER BALLOONS |
| 11.00 | 0.433 | 0.065 | 9 | 0.5 | 20.08 | 0.033 | 6.5-7.0 | |
| 12.27 | 0.483 | 0.065 | 9 | 0.5 | 25.01 | 0.033 | 7.0-7.5 | |

FIG. 2

DEVICE AND METHOD FOR AN IAB ASSIST WITH MULTIPLE BALLOONS

BACKGROUND OF THE INVENTION

1. Field of the Invention

This invention relates generally to cardiopulmonary support equipment, and more particularly, to intra-aortic balloon pumping devices and methods in which a working fluid is used to selectively inflate and deflate two or more intra-aortic balloons.

2. Description of the Related Art

Intra-aortic balloon catheters are used to reduce the burden on a still-beating heart, or to force blood to flow to the arteries, for example, the coronary arteries which are not receiving an adequate blood supply.

Intra-aortic balloon catheters typically consist of an intra-aortic balloon ("IAB"), an extension catheter and a connecting catheter which joins the balloon and the extension catheter. The extension catheter, connecting catheter and balloon are in fluid communication so that forcing gas through the connecting catheter causes the IAB to inflate and removing gas through the connecting catheter caused the IAB to deflate.

IAB catheters can be positioned in a patient's body using minimally-invasive catheterization procedures, rather than surgery. Typically, the furled intra-aortic balloon is inserted through a puncture wound in the groin into the patient's femoral artery and is advanced until it is disposed within the patient's descending aorta. Now the heart can be assisted by inflating and deflating the IAB in counterpulsation to the beating heart.

In designing IABs, a consideration is the benefits of minimizing the size of the wrapped membrane of the balloon which dictates the minimum size of the catheter that has to close off the puncture site in the femoral artery following the wrapped balloon membrane passage. The catheter should also be large enough to allow for the fast passage of gas, heretofore, described. All this usually causes limitation in the design and benefit to the patient.

First of all, certain percentage of LAB patients have atherosclerotic disease in their femoral and iliac arteries. That may lead to partial or near total occlusion of these vessels. That, in turn, may cause difficulties with inserting of an IAB and could provoke limb ischemia due to restricted distal blood flow. Similar complication may occur in smaller patients without this disease. It is estimated that 10–15% of IAB patients suffer from limb ischemia. Some patients are even completely denied the benefits of IAB therapy because of insertion difficulties.

A second problem is the removal of the IAB at the end of the procedure. A typical catheter has an OD of 9 to 10 Fr. After IAB removal, a clinician has to stop arterial bleeding which may not be a simple task. Pressure is usually applied to the groin area of the patient for several hours which is uncomfortable for the patient and present a constant risk of massive bleeding. Reduction of the OD of the inserted device from say 10 Fr or 11.5 Fr in the case of present insertion using a sheath to say 6 or 8 Fr will significantly improve hemostasis as known from PTCA and angiography procedures which use a smaller catheter and have a reduced time to hemostasis after the removal of the catheter.

Still another limitation of IAB therapy is the inability of the patient to move while receiving the IAB therapy. The reason for this is that movement often causes kinking of the IAB catheter which normally does not occur when small catheters, such as those used in PTCA and angiography are used.

Finally, the overall balloon volume of a catheter is limited by only a few standard volumes being presently offered for use.

An object of the present invention is therefore to overcome the various previously stated problems of the prior art by providing:

a. Smaller OD balloons to reduce the size of the insertion puncture;

b. An ability to mix and match different volume size balloons to obtain the exact volume needed without having to stock numerous sizes of balloons to obtain the proper volume, and c. Reducing the overall OD of the total catheter in order to facilitate the insertion of the catheter into arteries that are restricted in size for one reason or another while allowing for the maximum flow of blood through said arteries when the catheter is in place.

SUMMARY OF THE INVENTION

The present invention involves the use of two or more intra-aortic balloons which may be of different volume sizes used in conjunction with each other to reduce the overall size of the puncture site of insertion of each IAB balloon into the patient. The volume size of each balloon may also be different. The balloons, when in use, are in position, typically in the descending aorta of the patient, to displace a pre-determined volume by simultaneously inflation of said balloons. While it is preferred that each balloon be inflated by the same balloon pump, this is not necessary. In the following manner the total volume size of the combined balloons through mixing and matching various sizes of balloons can be almost endless and limited only by the size of the patient's aorta.

BRIEF DESCRIPTION OF THE DRAWINGS

FIG. 2 is a chart indicating the various dimension, volumes and wrap diameter that can be obtained with only a small number of individual sized balloons;

DESCRIPTION OF THE PREFERRED EMBODIMENTS OF THE INVENTION

The present invention is intended to improve the performance of an intra-aortic balloon catheter while also providing an optimization of the volume size of the balloon for both performance and insertion needs without creating the need for massive inventories of different size balloon volumes.

Figure 1:
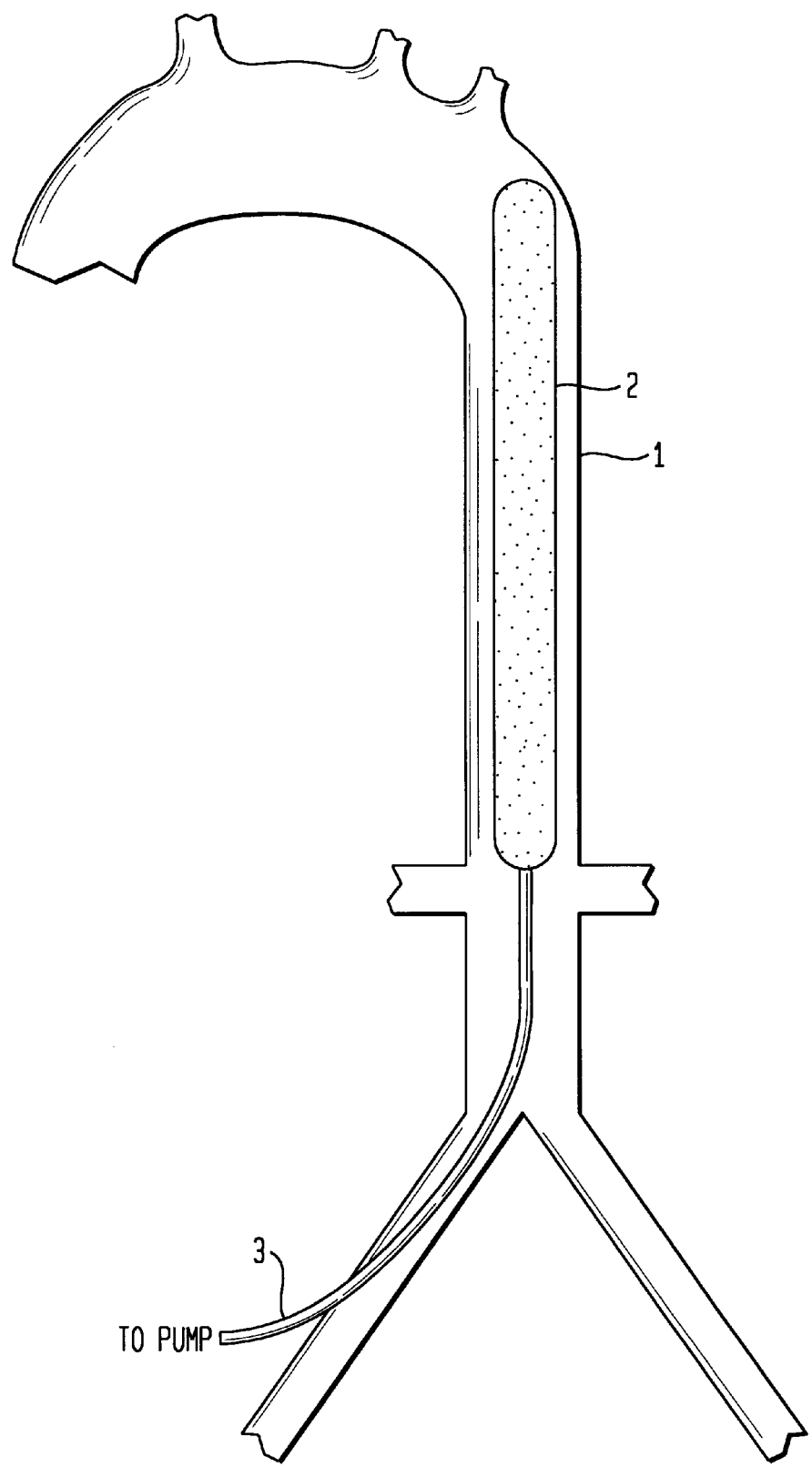
FIG. 1 is a plan side view of a conventional intra-aortic balloon catheter assembly.

Turning now to FIG. 1, Intra-aortic balloon catheters 1, consist of an intra-aortic balloon ("IAB") 2, an extension catheter 3 and a connecting catheter 4 which joins the balloon 2 and the extension catheter 3. The extension catheter 3, connecting catheter 4 and balloon 2 are in fluid communication so that forcing gas through the connecting catheter 4 causes the IAB 2 to inflate and removing gas through the connecting catheter 4 caused the LAB 2 to deflate as is known in the art and shown in more detail in U.S. Pat. No. 4,377,709 which is hereby incorporated by reference.

IAB catheters 1 can be positioned in a patient's body using minimally-invasive catheterization procedures, as is known in the art and as also shown in more detail in U.S. Pat. No. 4,377,709 which is hereby incorporated by reference, rather than surgery. Typically, the furled intra-aortic balloon 2 is inserted through a puncture wound 5 in the groin 6 into the patient's femoral artery 7 and is advanced until it is disposed within the patient's descending aorta 8. Now the heart 9 can be assisted by inflating and deflating the IAB 2 in counterpulsation to the beating heart 9.

Figure 3:
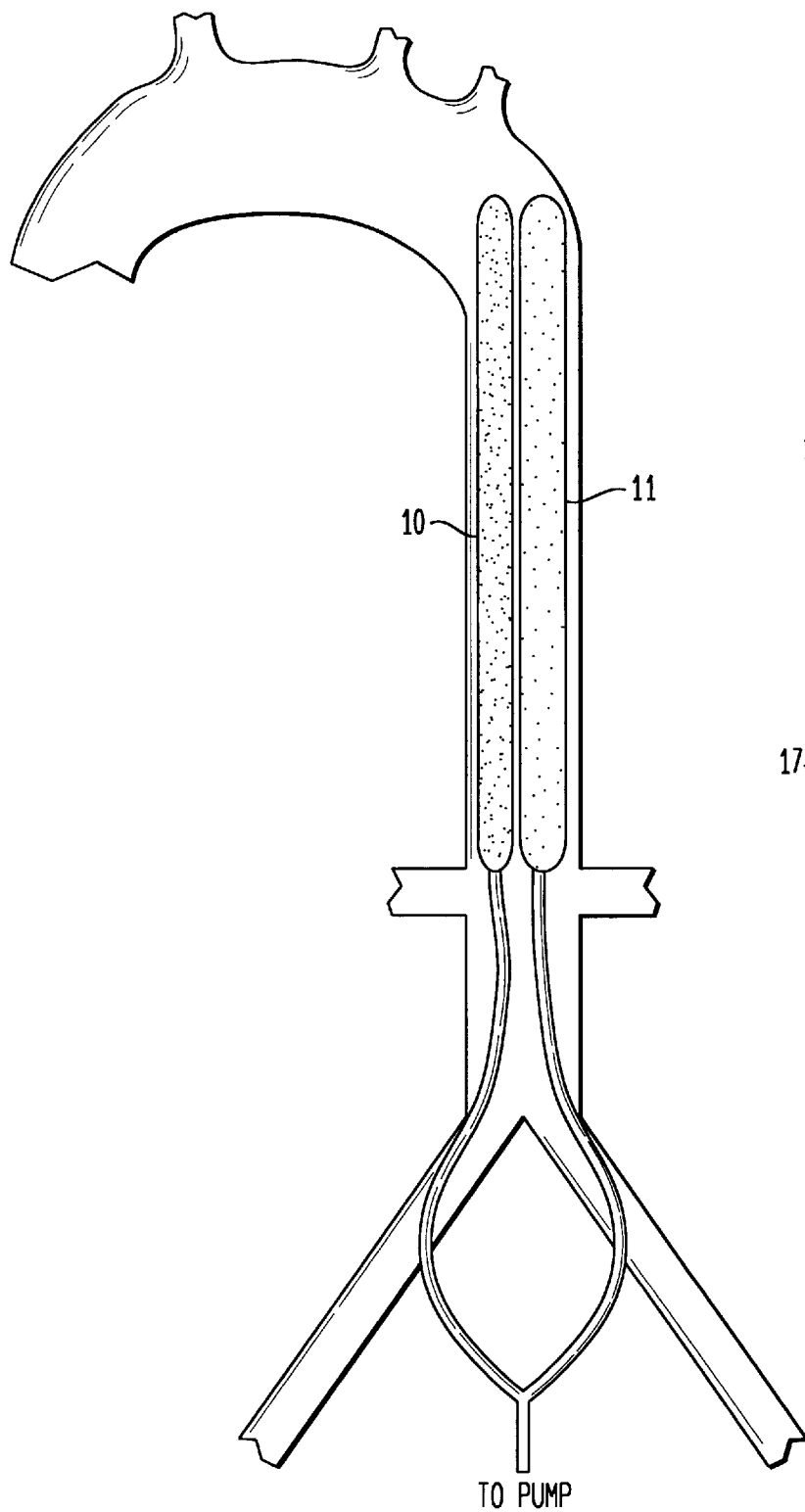
FIG. 3 is a side view of the multiple balloon placement in the aorta of the present invention.

Turning now to FIG. 3, in the present invention, the balloon 2 of FIG. 1 and the prior art, is replaced by two balloons 10 and 11 of different volume one being place in the right femoral artery 13 and the other being placed in the left femoral artery 14. While the balloons 10 and 11 depicted in FIG. 3 have a combined volume greater than the balloon 2 of FIG. 1, the combined volume of balloons 10 and 11 are such as to optimize the volume need for counterpulsation in the individual patient, while minimizing the OD of the puncture sites 15 and 16 of the right 13 and left 14 femoral arteries. This optimization also takes into consideration the available restriction in each individual patient's arteries for insertion of the catheter 1 and blood flow maximization through arteries 17 after positioning of the catheter 1.

Balloons 10 and 11 should usually be of similar length to optimize volume displacement in the descending aorta 8, but slight variations of size of the balloons 10 and 11 is not critical.

By using multiple balloons, such as balloons 10 and 11 of the present invention, one can see from FIG. 2 that a considerable amount of balloon volume combination may be obtained from a relatively few number of balloon volume sizes. In addition, FIG. 2 shows that the combination of balloons 10 and 11 can reduce the overall OD of each non-balloon portion from about 9.7 Fr. to 6 or 7 Fr. with the wrapped balloon 10 and 11 being reduced from about 10 Fr. to 7 or 8 Fr. without reducing the pumping volume of the overall system.

Figure 4:
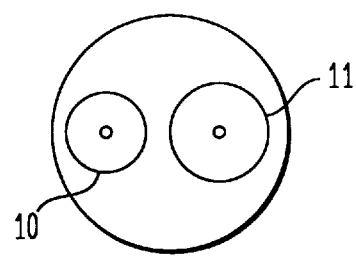
FIG. 4 is a top view of the multiple balloon placement in the aorta where the balloons are of a circular cross sectional area for use in the present invention and of a dual-lumen construction.
Figure 5:
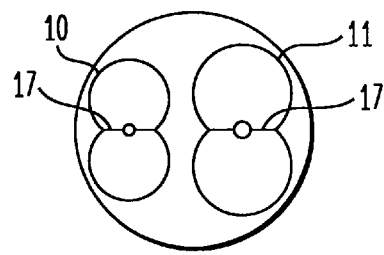
FIG. 5 is a top view of the multiple balloon placement in the aorta where the balloons are of a dual-lumen construction, and are of a non-circular cross sectional area for use in the present invention.
Figure 6:
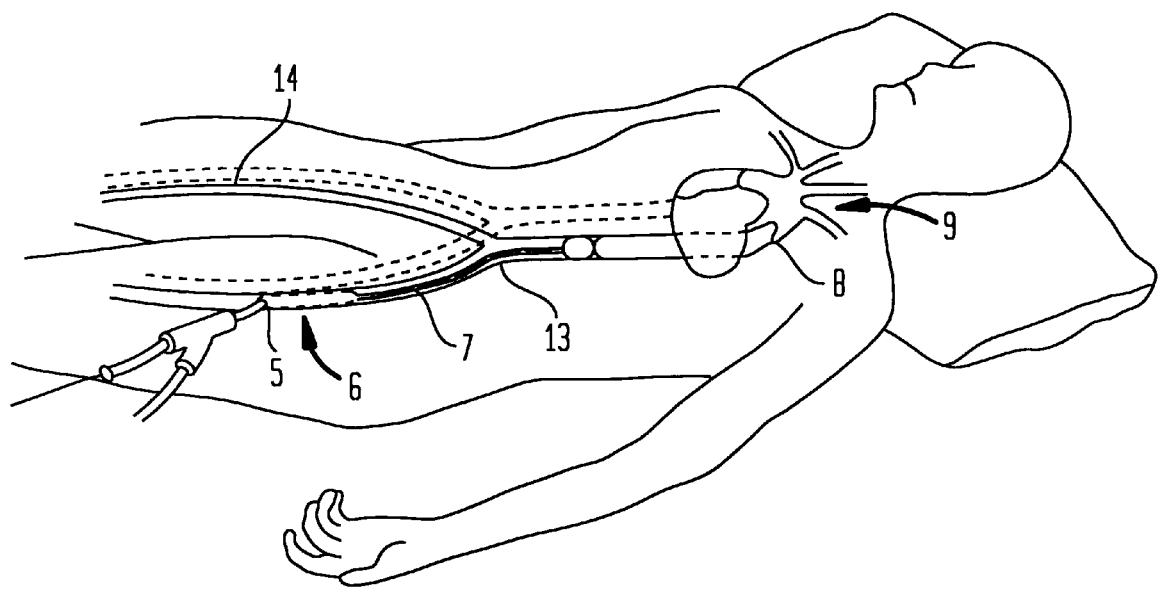
FIG. 6 is a prospective view of a patient with a conventional IAB inserted.

As shown in FIG. 3 the displaced volume of balloon 10 and 11 does not have to be equal. Balloons 10 and 11 may also have different ODs. Because the displaced volume and OD may be different, by mixing and matching balloons 10 and 11 one may obtain the exact volume displacement needed for a specific procedure without having to stock numerous sizes of balloons. While the balloons 10 and 11 of FIG. 4 have a circular cross section, this is not required as is shown by the balloons 10 and 11 of FIG. 5 which have a hemispherical shape with a middle septum 17 to keep balloons 10 and 11 from overexpanding.

There is also a possibility to have only one of the IABs with a dual-lumen construction for monitoring blood pressure. Typically, this will be the small balloon. The other balloon may be mounted on a single lumen catheter for further reducing the catheter OD.

Because of the smaller size of balloons 10 and 11 more insertion sites become available for use in the IAB therapy. The sites being femoral arteries 13 and 14, and subclavian arteries, 18 and 19 making for a potential of more than two balloons being ultimately used in the IAB therapy. Besides more sites being available for insertion, by using only the subclavian arteries 18 and 19 a patient during the procedure would have more mobility and the ability to sit up in bed because the inserting site is more conducive to this as well as the fact that the smaller catheters 1 are less prone to kinking. If fact, even if the femoral arteries 13 and 14 were used, because the smaller catheters are less subject to kinking, there is also the possibility of greater mobility to the patient. This is significant since is it well recognized that with increased mobility and the ability to sit up, the respiratory function is assisted and there are increases in the comfort of the patient which in return aides in the recovery process.

Because puncture site 5 is smaller, due to the fact that catheters 1 were smaller, there is less problems with obtaining hemostasis of a smaller puncture than a larger puncture and with products such VasoSeal on the market, the time period for the patient to become mobile and released from the facility of care is greatly reduced.

Because at least two balloons 10 and 11 are used, it is easier to wean the patient off of the IAB therapy. In the prior art the removal of balloon 2 meant that the patient no longer had the assistance of the IAB, whereas now, since only one balloon of balloons 10 and 11 need be removed at a time, the patient may still receive the assistance of the other balloon of smaller volume to assist in the heart blood pumping.

The same can be done at the insertion. In case of PTCA, one femoral artery is used for the PTCA catheter and the other IAB, once the PTCA is completed. The PTCA sheath is used for advancement of a second single-lumen IAB catheter.

It will be appreciated that the present invention is not intended to be limited to the drawings and embodiments discussed above. Numerous departures in construction, materials and operation can be made therefrom while still remaining within the scope of the claimed invention.

What is claimed is:

1. An intra-aortic balloon catheter assembly for assisting a heart in pumping blood, the assembly comprising:

a. at least two separate non-connected catheters;

b. an intra-aortic balloon membrane connected to each of the at least two catheters; and c. means for inflating and deflating the two separate, non-connected intra-aortic balloon membranes simultaneously in counterpulsation to the heart connected to the at least two catheters.

2. The assembly of claim 1 wherein the balloon membranes are of different displacement volumes.

3. The assembly of claim 2 wherein the balloon membranes along their length axis are of circular cross section.

4. The assembly of claim 2 wherein the balloon membranes are of non-circular cross section.

5. The assembly of claim 1 wherein the balloon membranes along their length axis are of circular cross section.

6. The assembly of claim 1 wherein the balloon membranes along their length axis are of non-circular cross section.

7. A method for intra-aortic balloon catheter counterpulsation for assisting a heart with a descending aorta in pumping blood, the method comprising the steps of:

a. placing at least two separate, non-connected catheters into the descending aorta of the heart, each of the at least two separate, non-connected catheters having an intra-aortic balloon membrane; and b. inflating and deflating the two separate, non-connected intra-aortic balloon membranes simultaneously in counterpulsation to the heart.

* * * * *

UNITED STATES PATENT AND TRADEMARK OFFICE
CERTIFICATE OF CORRECTION

PATENT NO.   : 5,910,103
DATED        : June 8, 1999
INVENTOR(S)  : Lawrence Saper, et. al.

It is certified that error appears in the above-identified patent and that said Letters Patent is hereby corrected as shown below:

Title page, item [75], inventors, the third inventor's name and address should read:
Boris Leschinksy, Waldwick, both of N.J.
Title page, under Attorney, Agent, or Firm, the second attorney's name should read:
Abraham Ronai.
Column 1, line 38, the seventh word should read "IAB" not "LAB".
      Line 64, the seventh word should read "IAB" not "LAB".
Title Page item [57], Abstract, the second word of the abstract should read "device", not Device".
Column 2, line 58, the fifth word should read "intra-aortic", not "Intra-aortic".
Column 4, line 12, insert the word –as— between "such" and "Vasoseal" so as to read: "such as Vasoseal".

Signed and Sealed this

Twenty-sixth Day of October, 1999

*Attest:*

Q. TODD DICKINSON

*Attesting Officer*     *Acting Commissioner of Patents and Trademarks*